United States Patent
Bringhurst et al.

(10) Patent No.: US 7,270,968 B2
(45) Date of Patent: Sep. 18, 2007

(54) PTH ANALOGS FOR RENAL OSTEODYSTROPHY AND RELATED USES

(75) Inventors: F. Richard Bringhurst, Walpole, MA (US); Paola Divieti, Arlington, MA (US); Harald Jüppner, Cambridge, MA (US)

(73) Assignee: The General Hospital Corporation, Boston, MA (US)

( * ) Notice: Subject to any disclaimer, the term of this patent is extended or adjusted under 35 U.S.C. 154(b) by 467 days.

(21) Appl. No.: 10/344,744

(22) PCT Filed: Aug. 14, 2001

(86) PCT No.: PCT/US01/25355

§ 371 (c)(1),
(2), (4) Date: Jul. 8, 2003

(87) PCT Pub. No.: WO02/14466

PCT Pub. Date: Feb. 21, 2002

(65) Prior Publication Data

US 2004/0014150 A1    Jan. 22, 2004

Related U.S. Application Data

(60) Provisional application No. 60/255,065, filed on Dec. 14, 2000.

(51) Int. Cl.
  *G01N 33/567*  (2006.01)
  *C12Q 1/68*  (2006.01)
  *C12N 15/63*  (2006.01)
  *C07H 21/02*  (2006.01)
  *C07H 21/04*  (2006.01)

(52) U.S. Cl. .......... 435/7.21; 435/6; 435/91.1; 435/325; 435/375; 435/455; 536/23.1; 536/23.2; 536/23.5; 536/24.5

(58) Field of Classification Search .......... 435/6, 435/91.31, 458, 455, 375, 7.21, 91.1, 325; 536/23.1, 24.5, 23.2, 23.5
See application file for complete search history.

(56) References Cited

OTHER PUBLICATIONS

Divieti et al., J. Bone & Mineral Res., vol. 13, No. 12, pp. 1835-1845 (1998).*
Lanske, B., et al., "Ablation of the PTHrP gene or the PTH/PTHrP receptor gene leads to distinct abnormalities in bone development," *J. Clin. Invest.* 104:399-407, American Society for Clinical Investigation (Aug. 1999).
Divieti, P., et al., "Conditionally immortalized primary murine calvarial osteoblasts: A model of PTH action and PTH/PTHRP receptor ablation," *Eur. J. Clin. Invest.* 25 (suppl. 2) :A46, Abstract No. 263, Oxford Blackwell Scientific Publications (1995).
Wysolmerski, J.J., and Stewart, A.F., "The physiology of parathyroid hormone-related protein. An emerging role as a developmental factor," *Annu. Rev. Physiol.* 60:431-460, Palo Alto Ca Annual Reviews (1998).

* cited by examiner

*Primary Examiner*—J Zara
(74) *Attorney, Agent, or Firm*—Sterne, Kessler, Goldstein & Fox P.L.L.C.

(57) ABSTRACT

The invention relates to a mammalian cell lacking type-1 parathyroid hormone (PTH)/parathyroid hormone-related peptide (PTHrP) receptor (PTH1R) activity and containing carboxyl-terminal parathyroid hormone receptor (CPTHR) activity. The invention also relates to a method of screening for agonists or antagonists for CPTHR.

4 Claims, 10 Drawing Sheets

PTH ANALOGS FOR RENAL OSTEODYSTROPHY AND RELATED USES

This application is a U.S. National Phase filing under 35 U.S.C. §371 of International Application PCT/US01/25355, which was filed on Aug. 14, 2001, and published in English as WO 02/14466 A2 on Feb. 21, 2002; this application also claims priority benefit to U.S. Provisional Application No. 60/255,065, filed Aug. 14, 2000.

STATEMENT AS TO RIGHTS TO INVENTIONS MADE UNDER FEDERALLY-SPONSORED RESEARCH AND DEVELOPMENT

Part of the work performed during development of this invention utilized U.S. Government funds. The U.S. Government has certain rights in this invention.

BACKGROUND OF THE INVENTION

1. Field of the Invention

The invention relates to a mammalian cell lacking type-1 parathyroid hormone (PTH)/parathyroid hormone-related peptide (PTHrP) receptor (PTH1R) activity and containing carboxyl-terminal parathyroid hormone receptor (CPTHR) activity. The invention also relates to a method of screening for agonists or antagonists for CPTHR.

2. Related Art

Parathyroid hormone (PTH) is the major physiologic regulator of blood calcium and phosphate, and it exerts potent effects upon cells in bone and cartilage (Heersche, J. N. M., et al., "Cellular Actions of Parathyroid Hormone on Osteoblasts and Osteoclasts Differentiation," in *The Parathyroids Basic and Clinical Concepts*, Bilezikian, J. P. et al., (eds.), Raven Press, New York, N.Y., pp. 83-91 (1994)). PTH and PTH-related peptide (PTHrP) activate a common G protein-coupled receptor, the type-1 PTH/PTHrP receptor (PTH1R) (Abou-Samra, A. B., et al., *Proc. Natl. Acad. Sci. USA* 89:2732-2736 (1992); Juppner, H., et al., *Science* 254:1024-1026 (1991); Juppner, H., *Bone* 25:87-90 (1999)). The PTH1R recognizes the highly conserved amino (N)-terminal domain of PTH (and the homologous N-terminus of PTHrP) and thus is fully activated by both PTH(1-34) and the intact hormone, PTH(1-84). Carboxyl(C)-fragments of intact PTH(1-84), such as PTH(39-84) or PTH(53-84), neither bind nor activate the PTH1R(Pines, M., et al., *Endocrinology* 135:1713-1716 (1994); Inomata, N., et al., *Endocrinology* 136:4732-4740 (1995); Bringhurst, F. R., et al., *Am. J. Physiol.* 255:E886-E893 (1988)). On the other hand, a possible physiologic role for this region of the hormone is indicated by observations that the amino acid sequence of the PTH C-terminal domain is highly homologous across species (Kbosla, S., et al., *J. Bone Miner. Res.* 3:689-698 (1988)); that PTH C-fragments, arising via both secretion from the parathyroid glands and proteolysis of PTH(1-84) in peripheral tissues, circulate in blood at levels much higher than those of the intact hormone; and that parathyroid secretion of PTH C-fragments is strongly regulated by serum calcium (D'Amour, P., et al., *Am. J. Physiol.* 251: E680-E687 (1986); Bringhurst, F. R., et al., *J. Endocrinol.* 122:237-245 (1989); Hanley, D. A., et al., *J. Clin. Invest.* 62:1247-1254 (1978); Martin, K., et al., *J. Clin. Invest.* 58:781-788 (1976); Dambacher, M. A., et al., *Clinical Sci.* 57:435-443 (1979)).

Studies with rat osteoblastic cell lines have shown that fragments from within the sequence PTH(35-84), which cannot activate PTH1Rs, regulate expression of alkaline phosphatase, osteocalcin, collagen α1 (I) and IGF binding protein-5 (Murray, T. M., et al., *Calcified Tissue International* 49:120-123 (1991); Nasu, M., et al., *Endocrine J.* 45:229-234 (1998); Takasu, H., et al., *Endocrinology* 137: 5537-5543 (1996)). Others have found direct effects of PTH C-fragments upon osteoclasts and osteoclast progenitors (Kaji, H., et al., *Endocrinology* 136:842-848 (1995)) and upon expression of collagen α1 (I) and α1 (X) expression in hypertrophic chondrocytes (Erdmamu, S., et al., *J. Cell Biol.* 135:1179-1191 (1996)). Several such fragments also were shown to induce cytosolic free calcium transients in human fetal hypertrophic chondrocytes (Erdmamn, S., et al., *Cell Calcium* 23:413-421 (1998)). Direct physical evidence of a putative receptor with binding specificity for C-terminal PTH sequences (CPTHR) was obtained by crosslinking of the peptide $^{125}$I-[Tyr$^{34}$]hPTH(19-84) (which does not bind to PTH1Rs) to 40 kD and 90 kD proteins in ROS 17/2.8 rat osteoblastic cells (Inomata, N., et al., *Endocrinology* 136: 4732-4740 (1995); Takasu, H., et al., *Endocrinology* 137: 5537-5543 (1996)).

Collectively, these observations indicate that CPTHRs are expressed normally in bone and cartilage and that they may be involved in physiologic control of cell differentiation and function in these tissues. The problem of renal osteodystrophy is of particular interest in this regard, as PTH C-fragments normally are cleared mainly by the kidneys and thus accumulate to very high levels in blood during renal failure (Bringhurst, F. R., et al., *Am. J. Physiol.* 255:ES86-E893 (1988); D'Amour, P., et al., *Am. J. Physiol.* 251:E680-E687 (1986); Martin, K., et al., *J. Clin. Invest.* 58:781-788 (1976); Dambacher, M. A., et al., *Clinical Sci.* 57:435-443 (1979)). Moreover hPTH(7-84) potently reduces the calcemic action of intact PTH(1-84) in a manner inconsistent with its low binding affinity to the PTH1R (Slatopolsky, E., et al., "A Novel Mechanism for Skeletal Resistance in Uremia," in *Program of the American Society of Nephrology Annual Meeting*, Miami, Fla. (Abstract) (1999)).

SUMMARY OF THE INVENTION

The invention relates to a mammalian cell lacking type-1 parathyroid hormone (PTH)/parathyroid hormone-related peptide (PTHrP) receptor (PTH1R) activity and containing carboxyl-terminal parathyroid hormone receptor (CPTHR) activity. The invention also relates to a method of screening for agonists or antagonists for CPTHR.

Different cell lines were tested for expression of CPTHRs by radioligand binding analysis at 15° C. using $^{125}$I-[Tyr$^{34}$] hPTH(19-84) as a tracer. Cells were plated at 100,000 cells/ml in 24 well plates and maintained in culture at 33° C. for 7 to 10 days. C cells expressed between 1,900,000 and 3,400,000 CPTHRs/cell while the F cells expressed less than 600,000 CPTHRs/cell as determined by Scatchard analysis (insert; ordinate=bound/free, abscissa=specific binding, pmoles/mg of protein). Specific binding is expressed as mean±standard deviation of triplicates in this representative experiment.

Figure 1:
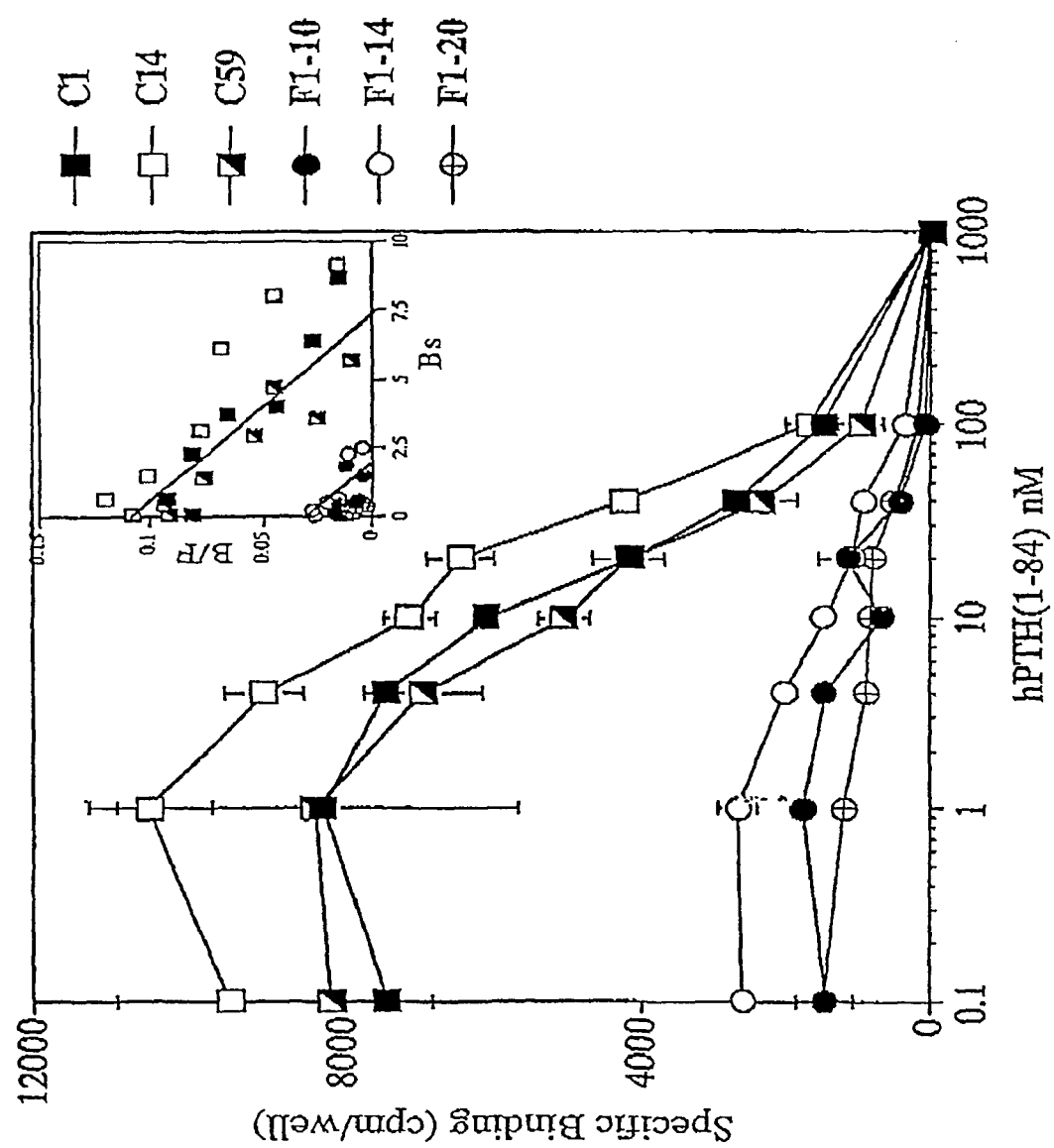
FIG. 1. Competitive ligand binding in C cells (OC1, OC14,and OC59) and F cells (F1-10, F1-14 and F1-20).
Figure 2:
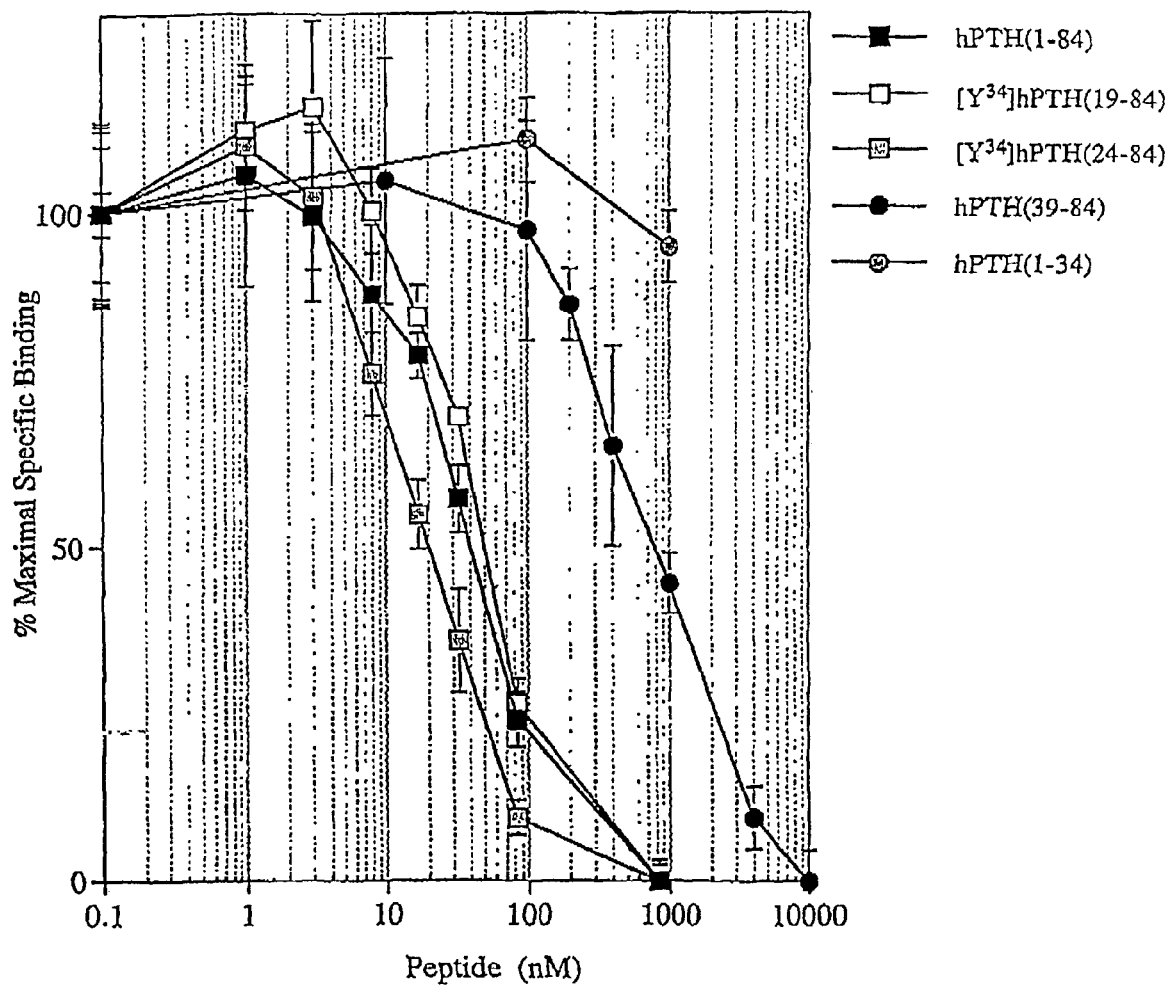

FIG. 2. Binding of N-terminally truncated human PTH fragments to CPTHRs in C59 cells The human PTH peptides shown were tested for their ability to displace the $^{125}$I-[Tyr$^{34}$]hPTH(19-84) tracer in C59 cells. Experiments were performed as described in FIG. 1.

Results are expressed as the percentage of maximal specific binding observed in the absence of competing ligand and are shown as mean±standard deviation of triplicates in this representative experiment.

Figure 3:
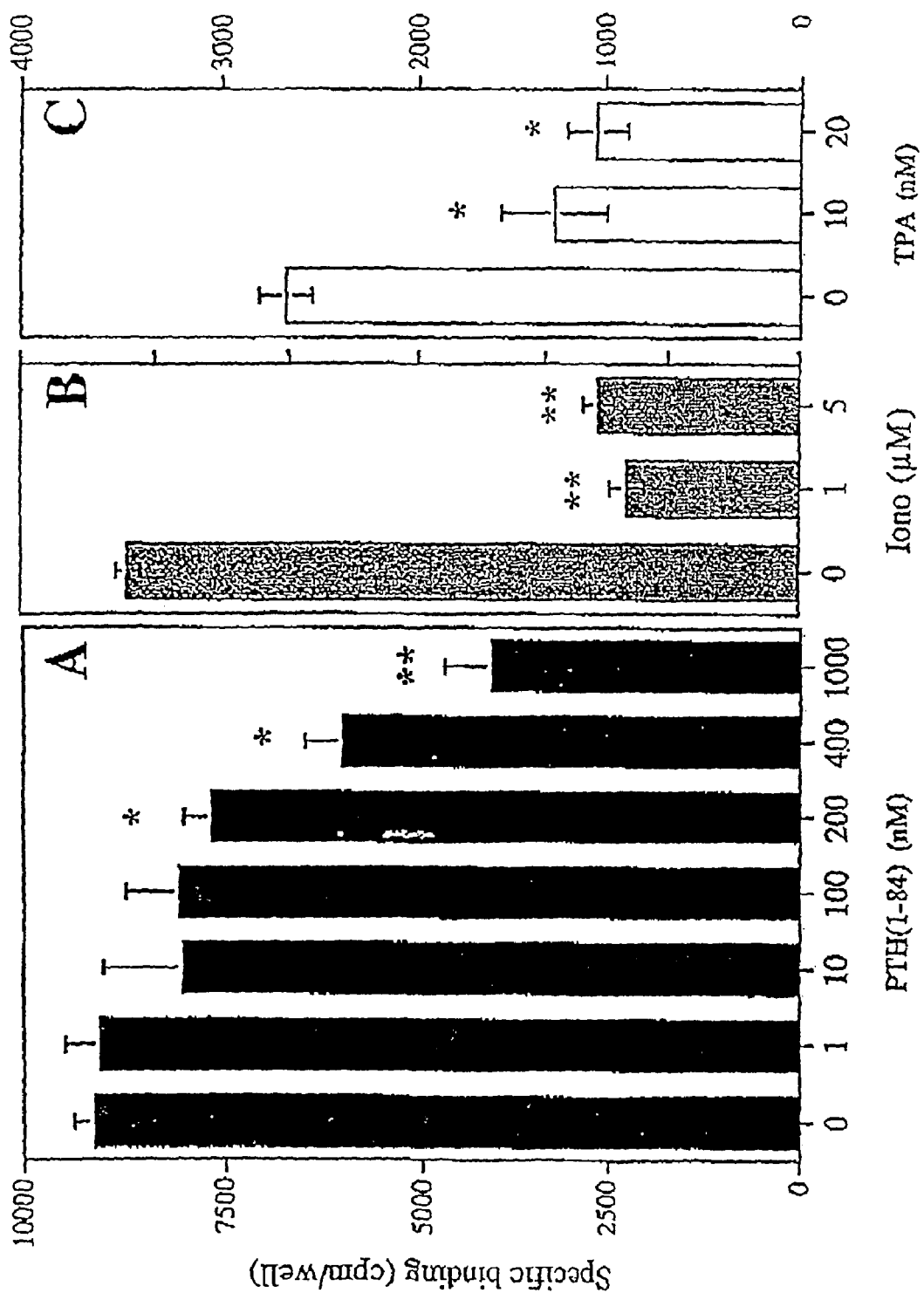

FIG. 3. Homologous downregulation of CPTHRs in C59 cells.

Cells were treated for 16 hv with the agent indicated and then rinsed three times with binding buffer and once with an acidic buffer (see Example 1), to completely remove any previously added PTH peptide from the receptor. Radioligand binding then was conducted using $^{125}$I-[Tyr$^{34}$]hPTH(19-84) as tracer±hPTH(1-84) as competing ligand in cells pretreated with A) hPTH(1-84) at the indicated concentrations (nM), B) ionomycin (µM), and C) the active phorbol ester TPA (nM). Specific binding, is expressed as mean ± standard deviation of triplicates. * p<0.05, ** P<0.01.

Figure 4:

FIG. 4. Connexin 43 expression at permissive and non-permissive temperature.

C59 cells (A and B) and F1-14 cells (C) were plated on glass coverslips at 72,000 cells/cm$^2$ and cultured at 33° C. (A) or at 33° C. for 2 days and then at 39° C. for 3-5 days (B and C) before staining for C×43 (see Example 1). Because of their osteocyte-like appearance, C cells were renamed "OC cells".

Figure 5:
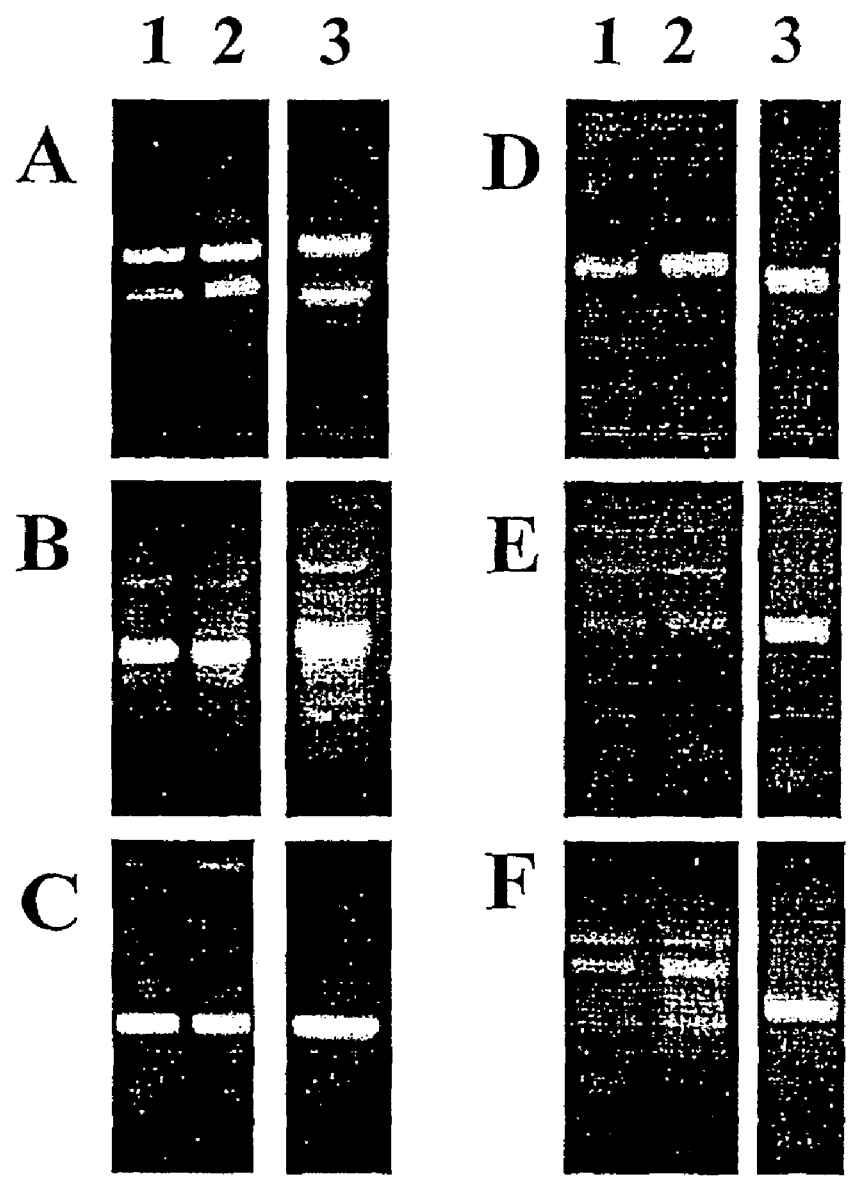

FIG. 5. Reverse-Transcriptase PCR analysis in OC cells and primary calvarial osteoblasts.

OC14 and OC59 (lanes 1 and 2) cells were cultured at 39° C. for 3-5 days before RNA extraction whereas primary calvirial osteoblast (lane 3) were cultured at 37° C. Expression of specific mRNAs was assessed by RT-PCR analysis, using 5 µg of total RNA (see Example 1). A) CD44 (upper band) and GAPDH (lower band); B) osteocalcin; C) osteopontin; D) collagen αI; E) alkaline pliosphatase; F) cbfa-1/osf-2.

Figure 6:
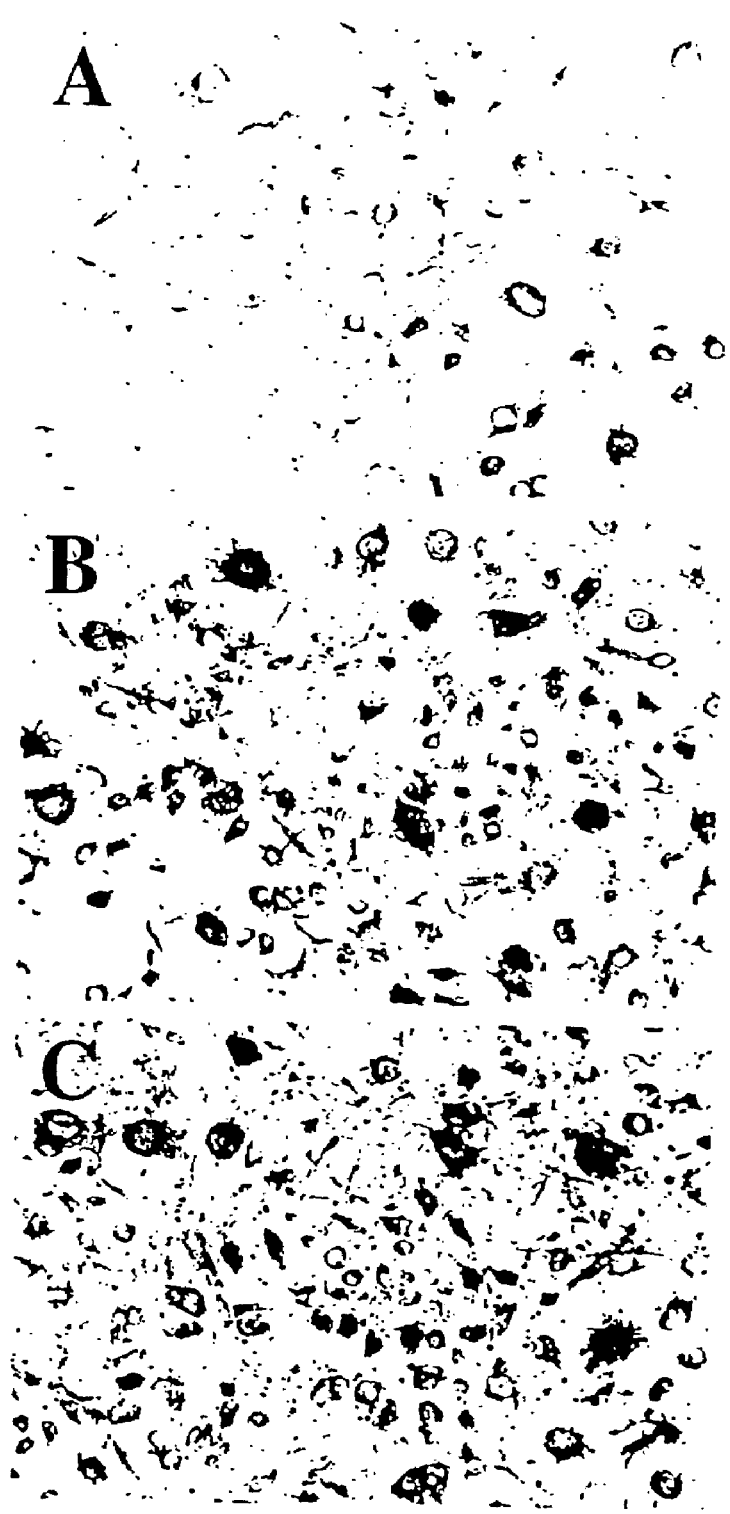

FIG. 6. Connexin 43 regulation by CPTHR ligands.

OC14 cells were plated on glass coverslips at 72,000 cells/cm$^2$, cultured at 33° C. for 2 days and then shifted at 39° C. for 3-5 days before stimulation with CPTHR ligands. OC14 cells were treated for 2 hr with (A) vehicle alone, (B) 100 nM hPTH(1-84) or (C) 1000 nm hPTH(39-84). Cells were fixed and stained for C×43 expression as described (see Example 1).

Figure 7:
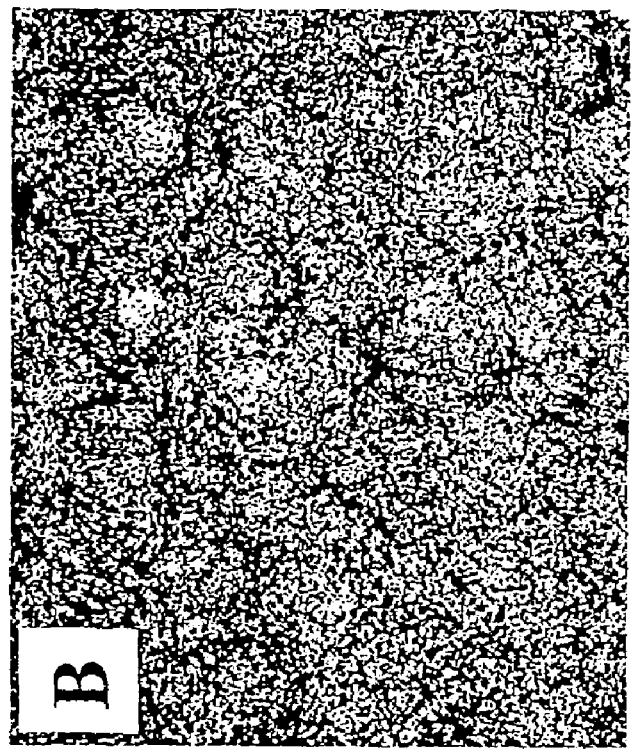
Figure 7:
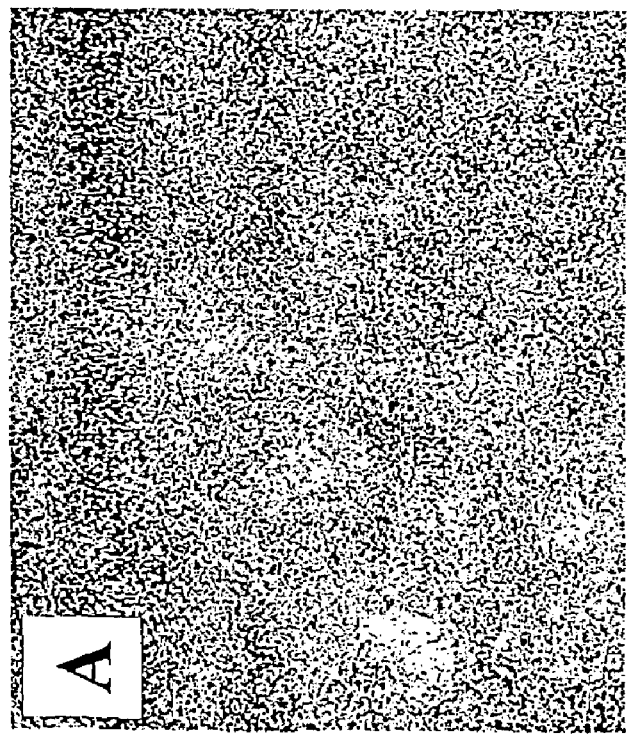

FIG. 7. Mineralization by OC14

OC14 cells were grown to confluence at 33° C. an 6 well-dishes and then maintained for an additional 4 weeks at 33° C. (A) or 39° C. (B) in the presence of 10 mM β-glycerophosphate and 50 µg/ml ascorbic acid before visualizing calcium phosphbate deposition by von Kossa staining. Magnification, 40×.

Figure 8:
Figure 8:
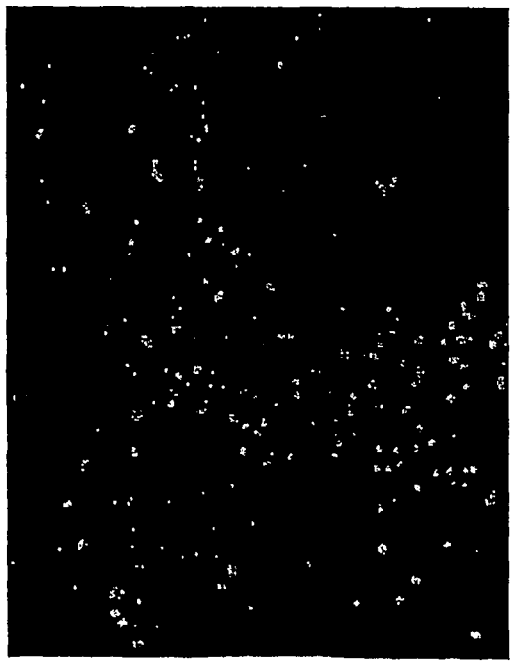
Figure 8:
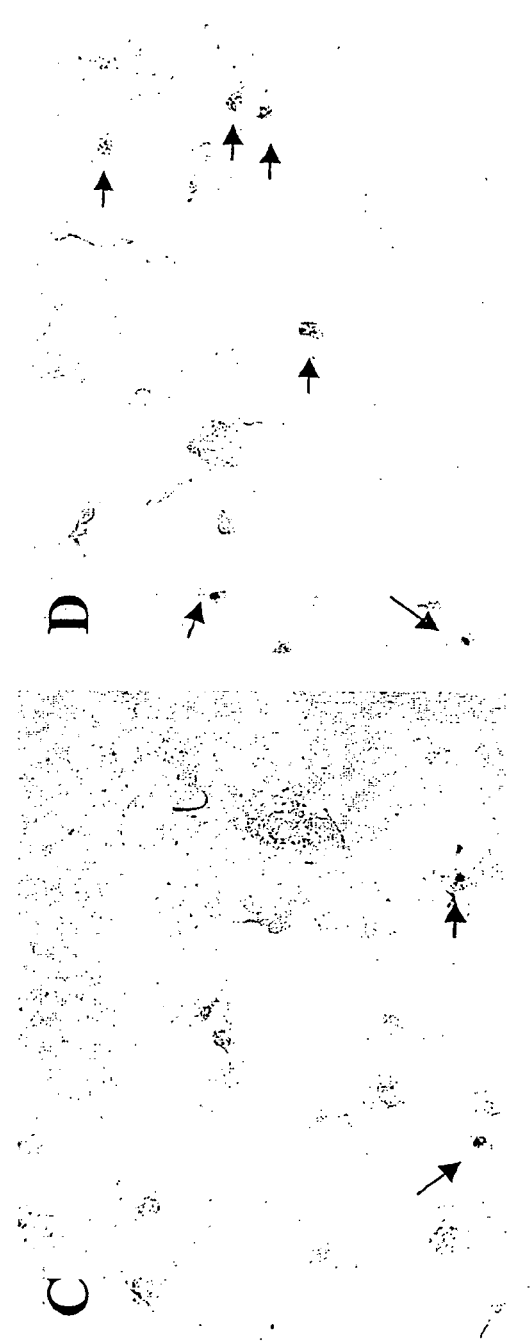

FIG. 8. Induction of apoptosis by PTH(1-84) in OC14 cells

Cells plated on glass coverslips and maintained at 33° C. for 33 days were shifted to 39° C. for 5-7 days before addition of 100 nM hPTH(1-84) (B, D) or vehicle alone (A, C) for 6 hr. At the end of the incubations, cells were fixed and stained with Hoechst 33258 (A and B) or for TUNEL (C and D) (see Example 1). Arrows indicate apoptotic cells. 200× magnification.

Figure 9:
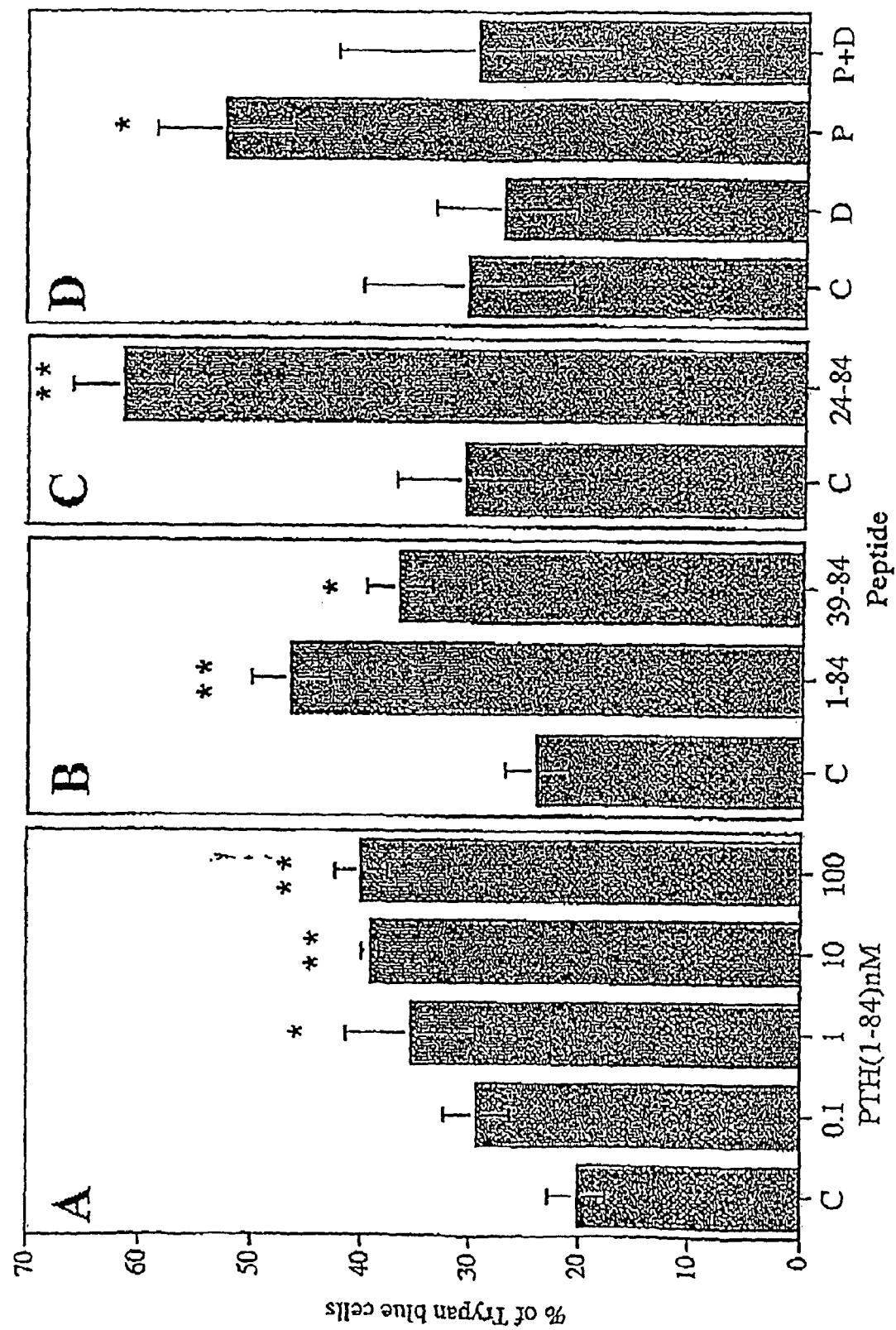

FIG. 9. Cell death induced by in PTH in OC14 cells.

OC14 cells were plated, cultured at 33° C. for 3 days and then incubated at 39° C. for 5-7 days before addition of PTH peptides for a further 16 hr, followed by trypan blue staining (see Example 1). A) Human PTH 1-84 dose response, B) Response to hPTH(1-84), 100 nM and hPTH(39-84), 1000 nM, C) Response to [Tyr$^{34}$]hPTH(24-84), 100 nM, D) Caspase dependance ("C"=controls) The Caspase-3 inhibitor DEVD ("D") was added 1 hr prior to addition of 100 nM hPTH(1-84) ("P"). Results are expressed as mean±SD of quadruplicate determinations of the percentage of nonvital trypan blue-stained cells. * p<0.05, ** p<0.01.

Figure 10:
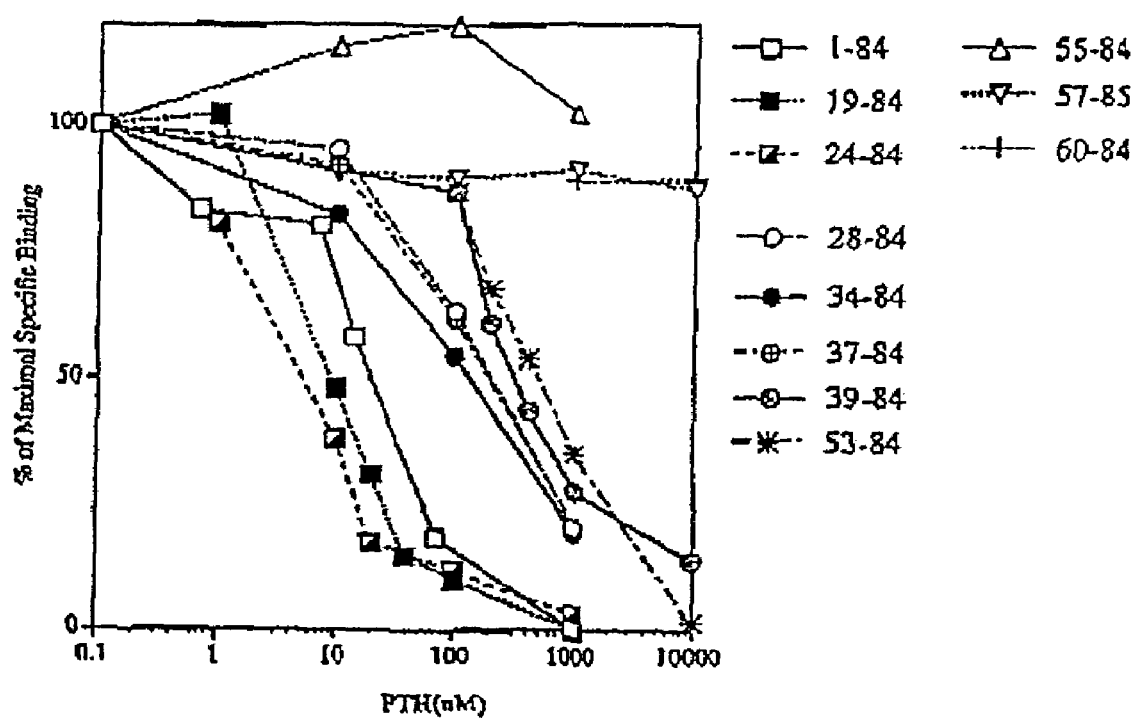

FIG. 10. $^{125}$I[Tyr$^{34}$]hPTH(19-84) radioligand binding in OC59 cells.

OC59 cells were incubated at 15° C. for 4 hr with $^{125}$I[Tyr$^{34}$]hPTH(19-84) tracer (150,000 cpn/well) plus the indicated competing human PTH peptides. Results are means of triplicates.

DETAILED DESCRIPTION OF THE PREFERRED EMBODIMENTS

The invention is directed to a mammalian cell lacking type-1 parathyroid hormone (PTH)/parathyroid hormone-related peptide (PTHrP) receptor (PTH1R) activity and containing carboxyl-terminal parathyroid hormone receptor (CPTHR) activity. In one embodiment, the cell is homozygous for the ablation of the PTH1R gene. In a further embodiment, the cell is an osteocyte. In yet a further embodiment, the cell is an osteoblast. An exemplary cell line, OC14, having an osteocytic phenotype, lacking PTH1R activity, and containing CPTHR activity, was deposited on Aug. 3, 2001 at the American Type Culture Collection, 10801 University Boulevard, Manassas, Va., 20110-2209, and given Accession Number PTA-3591.

The invention is also directed to a method of screening for agonists or antagonists for carboxyl-terminal parathyroid hormone receptor (CPTHR), said method comprising (a) contacting a mammalian cell lacking type-1 parathyroid hormone (PTH)/parathyroid hormone-related peptide (PTHrP) receptor (PTH1R) activity and containing CPTHR activity with a candidate compound; and (b) determining the rate of apoptosis of said cell, wherein an accelerated rate of apoptosis compared to said cell not contacted with a candidate compound indicates that said compound is an agonist for CPTHR, and wherein a rate of apoptosis equal to or less than said cell not contacted with a candidate compound indicates that said compound is an antagonist for CPTHR. In one embodiment, the cell is homozygous for the ablation of the PTH1R gene. In a further embodiment, the cell is an osteocyte. In yet a further embodiment, the cell is an osteoblast.

Preparation of Cells

In the invention, mammalian cells lacking PTH1R activity and containing CPTHR activity are prepared according to methods known in the art as embryonic stem cell knockout technology. In this method, a construct comprising a nucleotide sequence that is designed to decrease or suppress expression of a polypeptide, for example, PTH1R, encoded by an endogenous gene in one or more cells of a mammal is prepared. The nucleotide sequence used as the knockout construct is typically comprised of (1) DNA from some portion of the endogenous gene (one or more exon sequences, intron sequences, and/or promoter sequences) to be suppressed and (2) a marker sequence used to detect the presence of the knockout construct in the cell. The knockout construct is inserted into a cell containing the endogenous gene to be knocked out. The knockout construct can then integrate within one or both alleles of the endogenous gene, and such integration of the knockout construct can prevent or interrupt transcription of the full-length endogenous gene. Integration of the knockout construct into the cellular chromosomal DNA is typically accomplished via homologous recombination (i.e., regions of the knockout construct that are homologous or complimentary to endogenous DNA sequences can hybridize to each other when the knockout construct is inserted into the cell; these regions can then recombine so that the knockout construct is incorporated into the corresponding position of the endogenous DNA).

The knockout construct is typically transfected into stem cells derived from an embryo (embryonic stem cells, or "ES cells"). ES cells are undifferentiated cells that are capable of taking up extra-chromosomal DNA and incorporating it into their chromosomal DNA. Generally, the ES cells used to produce the knockout mammal will be of the same species as the knockout mammal to be generated. Thus for example, mouse embryonic stem cells will usually be used for generation of knockout mice.

The embryonic stem cell line used is typically selected for its ability to integrate into and become part of the germ line of a developing embryo so as to create germ line transmission of the knockout construct. Thus, any ES cell line that is believed to have this capability is suitable for use herein. The cells are cultured and prepared for DNA insertion using methods well known to the skilled artisan such as those set forth by Robertson (in: Teratocarcinomas and Embryonic Stem Cells: A Practical Approach, E. J. Robertson, ed. IRL Press, Washington, D.C. (1987)), by Bradley et al. (*Current Topics in Devel. Biol.* 20:357-371 (1986)) and by Hogan et al. (Manipulating the Mouse Embryo: A Laboratory Manual, Cold Spring Harbor Laboratory Press, Cold Spring Harbor, N.Y. (1986)).

Insertion (also termed "transfection") of the knockout construct into the ES cells can be accomplished using a variety of methods well known in the art including for example, electroporation, microinjection, and calcium phosphate treatment (see Lovell-Badge, in Robertson, ed., supra). A preferred method of insertion is electroporation.

The knockout construct DNA molecules to be transfected into the cells can first be linearized if the construct has previously been inserted into a circular vector. Linearization can be accomplished by digesting the DNA with a suitable restriction endonuclease selected to cut only within the vector sequence and not within the knockout construct sequence.

The isolated knockout construct DNA can be added to the ES cells under appropriate conditions for the insertion method chosen. Where more than one construct is to be introduced into the ES cells, the DNA molecules encoding each construct can be introduced simultaneously or sequentially. Optionally, homozygous knockout ES cells may be generated by adding excessive knockout construct DNA to the cells, or by conducting successive rounds of transfection in an attempt to achieve homologous recombination of the construct on both endogenous alleles.

If the ES cells are to be electroporated, the ES cells and knockout construct DNA are exposed to an electric pulse using an electroporation machine and following the manufacturer's guidelines for use. After electroporation, the cells are typically allowed to recover under suitable incubation conditions. The cells are then screened for the presence of the knockout construct.

Screening the ES cells can be accomplished using a variety of methods, but typically, one screens for the presence of the marker sequence portion of the knockout construct. Where the marker gene is an antibiotic resistance gene, the cells can be cultured in the presence of an otherwise lethal concentration of antibiotic. Those cells that survive have presumably integrated the knockout construct. If the marker gene is other than an antibiotic resistance gene, a Southern blot of the ES cell genomic DNA can be probed with a sequence of DNA designed to hybridize only to the marker sequence. If the marker gene is a gene that encodes an enzyme whose activity can be detected (e.g., beta-galactosidase), the enzyme substrate can be added to the cells under suitable conditions, and the enzymatic activity of the marker gene can be analyzed.

The knockout construct may integrate into several locations in the ES cell genome, and may integrate into a different location in each cell's genome, due to the occurrence of random insertion events; the desired location of insertion is within the endogenous gene sequence. Typically, less than about 1-10 percent of the ES cells that take up the knockout construct will actually integrate the knockout construct in the desired location. To identify those cells with proper integration of the knockout construct, chromosomal DNA can be extracted from the cells using standard methods such as those described by Sambrook et al., supra. This DNA can then be probed on a Southern blot with a probe or probes designed to hybridize to the knockout construct DNA digested with (a) particular restriction enzyme(s). Alternatively, or additionally, a specific genomic DNA sequence can be amplified by PCR with probes specifically designed to amplify that DNA sequence such that only those cells containing the knockout construct in the proper position will generate DNA fragments of the proper size.

After suitable ES cells containing the knockout construct in the proper location have been identified, the cells can be incorporated into an embryo. Incorporation may be accomplished in a variety of ways. A preferred method of incorporation of ES cells is by microinjection into an embryo that is at the blastocyst stage of development. For microinjection, about 10-30 cells are collected into a micropipet and injected into a blastocyst to integrate the ES cell into the developing blastocyst.

The suitable stage of development for the blastocyst is species dependent, however for mice it is about 3.5 days. The blastocysts can be obtained by perfusing the uterus of pregnant females. Suitable methods for accomplishing this are known to the skilled artisan, and are set forth for example by Bradley (in Robertson, ed., supra).

While any blastocyst of the right age/stage of development is suitable for use, preferred blastocysts are male and have genes coding for a coat color or other phenotypic marker that is different from the coat color or other phenotypic marker encoded by the ES cell genes. In this way, the offspring can be screened easily for the presence of the knockout construct by looking for mosaic coat color or other phenotypic marker (indicating that the ES cell was incorporated into the developing embryo). Thus, for example, if the ES cell line carries the genes for white fur, the embryo selected will preferably carry genes for black or brown fur.

An alternate method of preparing an embryo containing ES cells that possess the knockout construct is to generate "aggregation chimeras." A morula of the proper developmental stage (about 2 1/2 days old for mice) is isolated. The zona pellucida can be removed by treating the morula with a solution of mild acid for about 30 seconds, thereby exposing the "clump" of cells that comprise the morula. Certain types of ES cells such as the R1 cell line for mice can then be co-cultured with the morula cells, forming an aggregation chimera embryo of morula and ES cells.

A refinement of the aggregation chimera embryo method can be used to generate an embryo comprised of essentially only those ES cells containing the knockout construct. In this technique, a very early stage zygote (e.g., a two-cell stage zygote for mice) is given a mild electric shock. This shock serves to fuse the nuclei of the cells in the zygote thereby generating a single nucleus that has two-fold (or more) the DNA of a naturally occurring zygote of the same developmental stage. These zygotic cells are excluded from the developing embryo proper, and contribute only to forming accessory embryonic structures such as the extra-embryonic membrane. Therefore, when ES cells are co-cultured with the zygotic cells, the developing embryo is comprised exclusively of ES cells.

After the ES cells have been incorporated, the aggregation chimera or transfected embryo can be implanted into the uterus of a pseudopregnant foster mother. While any foster mother may be used, preferred foster mothers are typically selected for their ability to breed and reproduce well, and for their ability to care for their young. Such foster mothers are typically prepared by mating with vasectomized males of the same species. The pseudopregnant stage of the foster mother is important for successful implantation, and it is species dependent. For mice, this stage is about 2-3 days pseudopregnant.

Offspring that are born to the foster mother may be screened initially for mosaic coat color or other phenotype marker where the phenotype selection strategy (such as coat color, as described above) has been employed. In addition, or as an alternative, chromosomal DNA obtained from tail tissue of the offspring may be screened for the presence of the knockout construct using Southern blots and/or PCR as described above. The offspring that are positive for the knockout construct will typically be heterozygous, although some homozygous knockouts may exist, and can typically be detected by visually quantifying the amount of probe that hybridizes to the Southern blots.

If homozygous knockout mammals are desired, they can be prepared by crossing those heterozygous offspring believed to carry the knockout construct in their germ line to each other; such crosses may generate homozygous knockout animals. If it is unclear whether the offspring will have germ line transmission, they can be crossed with a parental or other strain and the offspring screened for heterozygosity. Homozygotes may be identified by Southern blotting of equivalent amounts of genomic DNA from mammals that are the product of this cross, as well as mammals of the same species that are known heterozygotes, and wild-type mammals. Probes to screen the Southern blots for the presence of the knockout construct in the genomic DNA can be designed as set forth above.

Other means of identifying and characterizing the knockout offspring are also available. For example, Northern blots can be used to probe mRNA obtained from various tissues of the offspring for the presence or absence of transcripts encoding either the knockout gene, the marker gene, or both. In addition, Western blots can be used to assess the level of expression of the knockout gene in various tissues of these offspring by probing the Western blot with an antibody against the protein encoded by the knockout gene, or an antibody against the marker gene product, where this gene is expressed. Finally, in situ analysis (such as fixing the cells and labeling with antibody) and/or FACS (fluorescence activated cell sorting) analysis of various cells from the offspring can be conducted using suitable antibodies to look for the presence or absence of the knockout construct gene product.

Immortalization of Cells

In the invention, mammalian cells lacking PTH1R activity and containing CPTHR activity can be conditionally immortalized by standard methods. These methods typically involve the chromosomal incorporation of a nucleic acid sequence (or sequences) into germ and/or somatic cells, the expression of which sequence is inhibited during normal animal development but which may be activated in isolated tissue culture. Preferably, cells of the invention are conditionally immortalized with temperature sensitive (ts) mutants of the simian virus SV40 large T antigen (TAg). The utilization of this gene imparts a secondary level of control on gene activity during normal development, in that the protein encoded by this mutant gene is rapidly degraded It temperatures approximating those of the normal body temperature of a mouse. Cells which have been immortalized as such will proliferate indefinitely at temperatures which are permissive for expression of tsTAg, for example 33° C., but will revert to a non-dividing, end-stage cell at higher temperatures, for example 39° C.

Isolation of Cells

A mammalian cell lacking PTH1R activity and containing CPTHR activity can be isolated by known methods, preferably by enzymatic digestion of calvarial bones removed from fetuses whose PTH1R gene has been ablated and which are transgenic for temperature-sensitive SV40 large T antigen (Divieti, P., et al., *J. Bone. Miner. Res.* 13:1835-1845 (1998)). PTH1R activity can be be detected by a variety of methods, including genomic PCR, cyclic AMP (cAMP) accumulation, and radioligand binding (Divieti, P., et al., *J. Bone. Mister. Res.* 13:1835-1845 (1998)). CPTHR activity can be detected by radioligand binding.

Screening Method

In the invention, a mammalian cell lacking PTH1R activity and containing CPTHR activity can be used to screen for agonists and antagonists for CPTHR by contacting the cell with a candidate compound, and determining the rate of apoptosis of the cell.

CPTHRs are expressed at uniquely high levels by osteocytes, which comprise 90% of all bone cells and play a pivotal role in maintaining normal bone structure and remodeling. Carboxyl (C)-terminal PTH fragments, which can bind to CPTHRs, but not PTH1Rs, circulate at excessive levels in renal failure, due mainly to impaired renal clearance of these fragments. C-terminal fragments normally comprise 60-80% of circulating PTH. This number is even higher in patients with renal failure. Levels of intact PTH (1-84) also are elevated in renal osteodystrophy, but less so than are C-terminal PTH fragments.

Most forms of renal osteodystrophy differ pathologically from the osteitis fibrosis that is seen in "pure" hyperparathyroidism, so something other than high levels of intact PTH is involved in the pathogenesis of most forms of renal osteodystrophy.

Interaction of synthetic model C-terminal PTH fragments with large numbers of CPTHRs expressed by clonal murine osteocytes in vitro leads to accelerated apoptosis of these osteocytes.

For these reasons, these osteocyte cell lines provide unique reagents with which to screen for molecules that interact with CPTHRs as agonists or antagonists.

Candidate antagonists are selected based upon their ability to interfere with the binding of intact PTH(1-84), and preferably contain domains which are critical for effective interaction between carboxyl (C)-terminal PTH fragments and CPTHRs in bone-derived cells, including PTH(24-27) and PTH(53-54).

Apoptosis can be determined by known methods, including staining the DNA of the cells with Hoechst dye 33258, the terminal deoxynucleotidyl transferase-mediated nick end labeling (TUNEL) reaction, and trypan blue staining.

Definitions

As used herein, "cell" is intended to refer to a cell of a human being or another mammal (e.g., guinea pig, rat, mouse, chicken, rabbit, pig, sheep, cattle, monkey, etc.), for example, splenic cell, nerve cell, glial cell, beta cell of pancreas, marrow cell, mesangial cell, Langerhans' cell, epidermic cell, epithelial cell, endothelial cell, fibroblast, fibrocyte, muscular cell, fat cell, immunocyte (e.g., macrophage, T cell, B cell, natural killer cell, mast cell, neutroplil, basophil, eosinophilic leukocyte, monocyte, etc.), megakaryocyte, synovial cell, chondrocyte, osteocyte, osteoblast, osteoclast, mammary gland cell, hepatocyte, or interstitial cells or precursor cells, stem cells or cancer cells thereof and the like.

As used herein, "lacking type-1 parathyroid hormone (PTH)/parathyroid hormone-related peptide (PTHrP) receptor (PTH1R) activity" is intended to refer to the condition of a cell whose gene encoding PTH1R has been removed or disrupted such that it is not expressed or is expressed at such low levels in the cell that it is unable to be activated by parathyroid hormone (PTH) and parathyroid hormone-related peptide (PTHrP).

As used herein, "containing carboxyl-terminal parathyroid hormone receptor (CPTHR) activity" is intended to the condition of a cell that undergoes accelerated apoptosis when contacted with intact parathyroid hormone (PTH) or carboxyl (C)-terminal fragments of PTH. This phase is also intended to refer to the condition of a cell that exhibits increased expression of Connexin-43 when contacted with intact parathyroid hormone (PTH) or C-terminal fragments of PTH.

As used herein, "homozygous" is intended to refer to the condition wherein two sequences of DNA at corresponding locations on homologous chromosomes are identical for one or more loci.

As used herein, "ablation" and "lockout" is intended to refer to the removal or disruption of an endogenous gene of a single cell, selected cells, or all of the cells of a mammal such that expression of the polypeptide, or portion thereof, encoded by the gene is reduced or eliminated.

As used herein, "PTH1R gene" is intended to refer to the sequence of DNA that comprises control and coding sequences necessary for the production of a type-1 parathyroid hormone (PTH)/parathyroid hormone-related peptide (PTHrP) receptor (PTH1R) or a precursor thereof. The PTH1R can be encoded by a full length coding sequence or by any portion of the coding sequence so long as the desired activity of the PTH1R is retained.

As used herein, "osteocyte" is intended to refer to a terminally differentiated osteoblast which is responsible for transducing shear and strain forces on bone into chemical signals that communicate this information to other osteocytes, osteoblasts, and osteoclasts.

As used herein, "osteoblast" is intended to refer to a cell that is responsible for the synthesis and mineralization of bone matrix.

As used herein, "agonist" is intended to refer to an agent or compound which binds to a receptor, thereby activating the receptor to carry out its normal function.

As used herein, "antagonist" is intended to refer to an agent or compound which reduces the rate of apoptosis of a mammalian cell which lacks type-1 parathyroid hormone (PTH)/parathyroid hormone-related peptide (PTHrP) receptor (PTH1R) activity and contains carboxyl-terminal parathyroid hormone receptor (CPTHR) activity PTH1R-expressing, as observed in response to an effective concentration of a known agonist, such as hPTH(1-84), administered simultaneously with or subsequent to the agent or compound.

As used herein, "contacting" is intended to refer to incubating the compound or agent under investigation with the appropriate cell of the invention.

As used herein, "apoptosis" is intended to refer to a regulated network of biochemical events which lead to cell death. It is a physiological process involved in cell differentiation, organ development and maintenance of cellular populations in multicellular organisms (Cohen, J. *J. Immunol. Today* 14: 126-130 (1993)). Furthermore, apoptosis is a reaction to various external stimuli and cell damage (e.g. induced by drugs). Apoptotic cells generally shrink and are phagocytosed by other cells. In contrast, necrotic cells are characterized by swelling, especially of the mitochondria which become dysfunctional, which usually results in cell lysis.

Molecular events characteristic of apoptotic cells include nuclear collapse with condensation of chromatin and loss of nucleoli. Later, the chromatin becomes fragmented into units of single or multiple nucleosomes which present a "ladder" appearance when separated by size on a gel matrix (Compton, M. M., *Cancer Metast. Rev.* 11:105-119 (1992)). Activation of an endogenous endonuclease causes the chromatin fragmentation. Intracellular RNA, especially mRNA, is also degraded early during apoptosis.

Apoptosis can be triggered in various ways, including virus infection, growth factor withdrawal, DNA damage resulting from irradiation, exposure to glucocorticoids and certain chemotherapy drugs, or by signals such as TNF binding to its receptor or crosslinking the Fas receptor with anti-Fas antibodies (Cohen, J. *J. Immunol. Today* 14: 126-130 (1993); Williams, G. T., & Smith, C. A., *Cell* 74:777-779 (1993); Suda et al., *Cell* 75:1169-1178 (1993); Smith, et al., *Cell* 76:959-962 (1994); Lowe et al., *Nature* 362:847-849 (1993); Sentman et al., *Cell* 67:879-888 (1991)). The mechanisms of apoptosis are not fully understood, but the observed molecular changes that occur in apoptotic cells suggest that endogenous genes are responsible for apoptosis. The proteins produced from these induced genes lead to destruction of RNA and DNA ultimately leading to cell death.

The following examples serve to further describe and illustrate the invention, and are not meant in any way to limit the invention.

EXAMPLE 1

To establish a model system in which to address the possible functions of CPTHRs in bone, cells that expressed CPTHR in greatest abundance were isolated from cultures of enzymatically dispersed primary fetal murine calvarial cells. To eliminate confounding effects of co-expressed PTH1Rs, these cells were derived from fetuses in which most exons encoding the PTH1R had been completely knocked out by gene targeting (Divieti, P., et al, *J. Bone. Miner. Res.* 13:1835-1845 (1998); Lanske, B., et al., *Science* 273:663-666 (1996)). These homozygous mice also were bred to ubiquitously express a transgene encoding a temperature-sensitive mutant SV40 large-T antigen (tsTAg), which enabled isolation of conditionally transformed clonal cell lines (Divieti, P., et al., *J. Bone. Miner. Res.* 13:1835-1845 (1998)).

The subpopulation of calvarial-derived bone cells that expresses the highest levels of CPTHRs exhibits morphologic and molecular features characteristic of osteocytes, the most terminally differentiated cells of the osteoblast lineage (Nijweide, P. J., et al., "The Osteocyte," in *Principle of Bone Biology*, Bilezikian, J. P., et al., (eds.), Academic Press, New York, N.Y., pp. 115-126 (1996); Kato, Y., et al., *J. Bone Miner. Res.* 12:2014-2023 (1997)). The inventors have further discovered that these cells undergo accelerated apoptosis when incubated with intact PTH and amino-terminal PTH fragments.

Materials and Methods

Materials

Culture media were obtained from the Media Kitchen (Pediatric Surgery, Massachusetts General Hospital, Boston, Mass., U.S.A.), other tissue culture reagents were purchased from Gibco-BRL (Grand Island, N.Y., U.S.A.), and other reagents and chemicals were obtained from Sigma (St. Louis, Mo., U.S.A.) or Fisher Co (Pittsburgh, Pa., U.S.A.). Radioactive Na[$^{125}$I] was purchased from NEN Life Science Products (Boston, Mass., U.S.A.). Recombinant human (h)PTH(1-84), [Tyr$^{34}$]hPTH(19-84), [Tyr$^{34}$]hPTH(24-84), were gifts of Chugai Pharmaceutical Co. (Shizuoka, Japan) and [Asp$^{76}$]human PTH(39-94) was purchased from Peninsula (Belmont, Calif., U.S.A).

Cell Isolation and Culture

Gene targeting in embryonic stem (ES) cells was used to delete exons E2 through T which encode most of the PTH/PTHrP receptor (Lanske, B., et al., *Science* 273:663-666(1996). Briefly, a 4.5-kb BamHI fragment containing exon E1 of the PTH/PTHrP receptor gene was used as the 5' flanking region and subcloned by blunt end ligation into a similarly treated XhoI site in the pPNT plasmid. A 5.6-kb EcoRI fragment containing the 3' untranslated region of the PTH/PTHrP receptor gene, cloned into the EcoRI polylinker site of pPNT, was used as the 3' flanking region. The resulting targeting vector was linearized at a unique NotI site in the pPNT backbone for electroporation of ES cells. Antibiotic resistant ES clones were selected and analyzed by Southern (DNA) blot analyses with an external intronic 0.9-kcb SacI-XhoI fragment at the 5' end of the gene. Positive clones were injected into recipient blastocyst-stage embryos to generate chimeras.

Cells were isolated by enzymatic digestion from calvarial bones of 18.5 day-old tsA58(+)/PTH1R(−/−) fetuses, produced by mating C57/B16 mice doubly heterozygous for deletion of the PTH1R gene, and for a transgene encoding the temperature-sensitive T antigen (tsA58TAg) (Immortomouse®, available from Charles River Laboratories, Wilmington, Mass.), as previously described(Divieti, P., et al., *J. Bone. Miner. Res.* 13:1835-1845 (1998)). Briefly, the calvarial bones were dissected aseptically and sequentially digested in 0.5 ml of α-Minimum Essential Medium (αMEM) containing 0.1% bovine serum albumin (BSA) 1 nM $CaCl_2$ and 1 mg/ml of collagenase (type I and II; ratio 1:3) (Worthington Biochemical Corporation, Freehold, N.J., U.S.A.). Bones were sequentially digested 6 times for 20 min each at 37° C. on a rocking platform at 90 oscillations per minute under 5% $CO_2$, in air. Cells were cultured at 33° C. in a humidified atmosphere (95% air/5% $CO_2$) using growth medium [α-ME containing 10% fet al bovine serum (FBS) (lot#1011961 Gibco-BRL) and 1% penicillin-streptomycin (PS)].

HeLa and BHK21 cells were obtained from Dr. Joel Habener (Molecular Endocrine Unit, Massachusetts General Hospital, Boston, Mass.) and NIH-3T3 cells were provided by Dr. Gino Segre (Endocrine Unit, Massachusetts General Hospital, Boston, Mass.). MS-1 cells are clonal conditionally immortalized murine bone marrow stromal cells previously isolated (Liu, B. Y., et al., *Endocrinology* 139:1952-1964 (1998)).

Radioligand Binding

The [Tyr$^{34}$]hPTH(19-84) peptide was radioiodinated with Na[$^{125}$I](2000 Ci/mmol) by the chloramine-T method and purified by HPLC, as previously described (Inomata, N., et al., *Endocrinology* 136:4732-4740 (1995)). For binding experiments, cells (100,000 cells/ml) were plated in 24-well dishes and cultured at 33° C. for 7 to 14 days. Confluent monolayers then were washed with 0.5 ml binding buffer [100 mM NaCl, 5 mM KCl, 2 mM $CaCl_2$, 50 mM Tris-HCl (pH 7.8) plus 5% heat-inactivated horse serum] before incubation with $^{125}$I-[Tyr$^{34}$]hPTH-(19-84) (100,000-200,000 cpm/well) in 0.5 ml binding buffer for 4 h at 15° C. Receptor number was ascertained by Scatchard analysis, using [Tyr$^{34}$]hPTH-(19-84) or hPTH(1-84) as competing ligand. Cellular protein was measured using the BCA protein assay lit (Pierce, Rockford, Ill., U.S.A.) and was found to average 0.33 Mg/$10^6$ cells and 0.47 Mg/$10^6$ cells for F cells aud C cells, respectively. In some experiments, cells were washed with acidic buffer (50 mM glycine, 150 mM NaCl, pH 4.0) to remove residual bound ligand, prior to addition of radioligand.

Cyclic AMP Accumulation

Cells were rinsed twice with assay buffer (135 mM NaCl, 6 mM KCl, 1 mM $MgCl_2$, 2.8 mM glucose, 1.2 mM $CaCl_2$), and 20 mM HEPES, pH 7.4) and then incubated for 15 min at 37° C. with the same buffer containing 0.1% heat inactivated BSA, 1 mM isobutylmethylxanthine (IBMX), and agonist, conditions under which cAMP accumulation was found to be linear with time for at least 15 min. The buffer then was rapidly aspirated, the plates were frozen in liquid nitrogen, and the frozen cells were subsequently thawed directly into 0.5 ml of 50 mM HCl. Cell-associated cAMP in the acid extracts was measured using an RIA kit (NUN Life Science Products, Boston, Mass., U.S.A.). Results were expressed as picomoles of cAMP produced per well over 15 min.

Reverse-Transcriptase Polymerase Chain Reaction (RT-PCR) Analysis

Total RNA was extracted from 6-well dishes using the TRIreagent® method (Sigma) and quantified by ultraviolet absorbance. RT-PCR was performed on total RNA using the SuperScript® Preamplification System from Life Technologies (Gibco BRL) with a Peltier Thermal Cycler (MJ Research, Watertown, Mass., U.S.A.). Subsequent PCR was performed using pairs of specific primers and optimized conditions for each, as previously reported (Kato, Y., et al., *J. Bone Miner. Res.* 12:2014-2023 (1997); Liu, B. Y., et al., *Endocrinology* 139:1952-1964 (1998)). The PCRproducts were electrophoresed on 1.5% agarose gels and visualized using ethidium bromide staining.

Von Kossa Staining

Cells, plated in 6-well dishes, were maintained at 33° C. for 3-4 days, until confluent, before refeeding with fresh medium containing 10 mM β-galactophosphate (β-GP) and 50 µg/ml ascorbic acid and transferring to nonpermissive conditions (39° C.). Cells were refed with fresh medium twice per week. After 3-4 weeks the presence of mineralized nodules was assessed by von Kossa staining, as previously described (Divieti, P., et al., *J. Bone. Miner. Res.* 13:1835-1845 (1998)). Briefly, after fixation in 95% ethanol for 15 min at 37° C., cells were gradually rehydrated with water and stained with 5% silver-nitrate for 1 h at 37° C. Cells were then exposed to incandescent light (100 W) for 15-30 min.

Western Blot Analysis and Immunocytochemical Staining

For Western blot analysis, cells were plated in 6-well dishes and cultured at appropriate temperatures in growth medium. At confluence, the cells were washed twice with PBS and lysed by incubation in ice-cold RIPA buffer (50 mM Tris-HCl, pH 7.2, 150 mM NaCl, 1% NP-40, 0.5% sodium deoxycholate) for 5 minutes at 4° C. The lysates were centrifuged at 14,000 rpm for 10 min, after which the supernatants were collected and passed ten times through a 22 gauge needle. Proteins were separated by SDS-PAGE (7% acrylamide gel) and tranisblotted to Hybond nitrocellulose membranes using standard procedures. Membranes were first blocked for 30 min at room temperature in Tris-buffered saline, pH 8.0, plus 0.05% TWEEN®-20 (TBS-T) with 5% powdered milk solution, iimmiuniostained for 60 min with 1:1000 dilution of first antibody specific for murine connexin 43 (C×43) (Zymed Laboratory, Inc., San Francisco, Calif., U.S.A.). The membranes were washed several times in TBS-T and then incubated for 60 min with the second antibody/enzyme conjugate (HRP antimouse IgG diluted 1:1500). Immunoreactive bands were detected by enhanced chemiluminesence assay (ECL, Amersham Life Science Inc.) according to the manufacturer's instructions.

For Immunocytochemical analysis, cells were plated on glass chamber slides at 72,000 cells/cm$^2$, cultured for two days at 33° C. and then shifted for an additional 4-6 days at 39° C. Cells were treated with vehicle alone (0.1% TFA) or with the appropriate hormone for the time indicated. The immunocytochemical staining was performed as previously described (Kato, Y., et al., *J. Bone Miner. Res.* 12:2014-2023 (1997)). Briefly, cells were fixed in 3% paraformaldehyde/2% sucrose in PBS and permeabilized for 5 min. with 0.05% Triton-X 100 diluted in PBS. The fixed slides were blocked in 5% BSA in TBS-T buffer for 2 h at room temperature. The cells then were incubated with a 1:125 dilution of anti-C×43 monoclonal antibody for 30 min at room temperature. The bound antibody was detected using a Vectastain ABC kit, followed by staining with VIP substrate according to manufacturer's instructions (Vector Laboratories, Burlingame, Calif.). Counter staining was performed using 0.5% methyl green. In some cases, anti-C×43 antibody was omitted to control for non-specific staining.

Apoptosis

The pyknotic fragmentation of nuclei typical of apoptotic cells was detected using Hoechst-33258 fluorescent dye (Sigma Co., St. Louis, Mo., U.S.A.). Briefly, cells were cultured on glass coverslips and maintained in culture at nonpermissive conditions for 4-6 days in (α-MEM supplemented with 2-5% of FBS and 1% PS. After exposure to the test hormones for 6 hr, culture medium was aspirated and cells were fixed in 4% paraformaldehyde in phosphate buffered solution and then stained with Hoechst-33258 (2.5 mg/mL) for 5 min at room temperature. Cells were washed and mounted with glycerol-PBS (9:1, v/v). The stained nuclei were visualized by fluorescence microscopy using DAPI filter. In some experiments, apoptotic cells were detected by the terminal deoxynucleotidyl transferase-mediated nick end labeling (TUNEL) reaction, using the In Situ Cell Death Detection Kit from Roche Molecular Biochemicals (Indianapolis, Ind., U.S.A.) following the manufacturer's instruction.

Trypan blue staining was used for routine quantification of cell death, as it previously was shown to correlate well with apoptosis in an osteocytic cell line (Jilka, R. L., et al., *J. Clin. Invest.* 4:439-446 (1999)). Briefly, cells were plated at 50,000 cells/well in 24-well dishes at 33° C. and shifted to nonpermissive conditions (39° C.) after 2 days. Cells were grown at 39° C. for an additional 4-6 days in α-MEM supplemented with 2.5% of FBS and 1% PS and then treated with different hormones for additional 16-18 hr. Non-adherent cells were combined with adherent cells that were released from the cultures with trypsin-EDTA, centrifuged and resuspended in 0.1% trypan blue solution. The percentage of cells exhibiting both nuclear and cytoplasmic staining was determined using a hemocytometer.

Statistical Analysis

All results were expressed as the mean±standard deviation (SD). Each experiment was repeated at least twice. Significance of differences between treatment and control groups was assessed by Student's t-test using Bonferroni correction.

Results

Cell Isolation and C-PTH Radioligand Binding

Primary mixed calvarial cells, "F1", were isolated by sequential collagenase digestion from a PTH1R(−/−)/tsAg (+) animal, as previously described (Divieti, P., et al., *J. Bone. Miner. Res.* 13:1835-1845 (1998)). It was reported previously that these cells, and osteoblastic subclones derived from them, did not express PTH1Rs, or any other species of Gs-linked PTH receptors, as indicated by (a) the absence of PTH1R DNA by genomic PCR, (b) no detectable cAMP response to hPTH(1-34), hPTH(1-84) or hPTHrP(1-36) and (c) no specific binding of the $^{125}$I-[Nle$^{8,18}$, Tyr$^{34}$]bPTH(1-34)NH$_2$ radioligand. Cells expressing CPTHRs were present in this heterogeneous cell preparation, however, as demonstrated in preliminary experiments by the specific displacement of $^{125}$I-[Tyr$^{34}$]hPTH(19-84) radioligand by intact hPTH(1-84).

To identify cells with high expression of CPTHRs, single colonies were isolated from the mixed F1 population by limiting dilution and then screened for specific binding of $^{125}$I-[Tyr$^{34}$]hPTH(19-84). Among twenty subclones isolated, all of which bound the radioiodinated C-PTH tracer, three clones, initially designated OC1, OC14 and OC59 (i.e., "C cells") were selected for further characterization on the basis of their distinctly high specific binding of the $^{125}$I-[Tyr$^{34}$]hPTH(19-84) radioligand. Like the previously described osteoblastic clonal cell lines (Divieti, P., et al., *J. Bone. Miner. Res.* 13:1835-1845 (1998)), these three "C cells" did not express any other species of Gs-linked PTH receptors, as demonstrated by the absence of a detectable cAMP response to either hPTH(1-34) or hPTH(1-84). Comparison of the CPTHR binding of these C cells with those of the previously described osteoblastic ("F") cells, which had been selected for high alkaline phosphatase activity rather than for CPTHR binding (Divieti, P., et al., *J. Bone. Miner. Res.* 13:1835-1845 (1998)), is shown in FIG. 1. The amount of total radioactivity bound averaged 14.4±3.2% for the three C cell clones, vs. 2.98±0.51% for the three previously reported F cell lines. Nonspecific binding, assessed in the presence of 10$^{-6}$ M hPTH(1-84), was 2.8±1.2% and 1.04±0.15% for the C and F cell clones, respectively. As assessed by Scatchard analysis, CPTHR expression by C cells ranged from 1,900,000 to 3,400,000 sites/cell on the C cells but was less than 600,000 sites/cell on the F cells (ranging from 200,000 to 600,000) (FIG. 1, insert).

To identify the region(s) of the PTH molecule required for binding to the CPTHR, competitive displacement analysis was performed using various anion-terminally truncated human PTH fragments. As shown in FIG. 2, hPTH(1-84) displaced the $^{125}$I-[Tyr$^{34}$]hPTH(19-84) radioligand as effectively as [Tyr$^{34}$]hPTH(19-84) (IC$_{50}$=20-50 nM for both). Binding by the fragment [Tyr$^{34}$]hPTH(24-84) also was equivalent to that of hPTH(1-84), whereas the shorter peptide hPTH(39-84) was much less potent, with an $IC_{50}$ in the range of 500-700 nM. The hPTH(1-34) peptide did not displace the tracer significantly at concentrations up to 1000 nM.

Regulation of CPTHR Expression

Expression of CPTHRs, as assessed by specific $^{125}$I-[Tyr$^{34}$]hPTH(19-84) binding, was downregulated in a concentration-dependent manner by pretreatment of C59 cells for 16 h with hPTH(1-84) (FIG. 3A). Binding was reduced 19±5% and 66±7% by preincubation with hPTH(1-84) at concentrations of 200 nM and 1000 nM, respectively. To assure that this change was due to a reduction in total binding sites and not simply to persistent receptor occupancy by preadministered hPTH(1-84), cells were rinsed, prior to radioligand addition with acidic buffer that was found in preliminary experiments to completely and reversibly remove previously bound radioligand. CPTHR binding also was downregulated following preincubation for 16 h in the presence of calcium ionophore (ionomycin, 1 μM) or active phorbol ester (TPA, 10 nM), which reduced specific binding by 71±3% and 48±12%, respectively. The effects of these drugs were at least partly reversible, as radioligand binding returned to 100% and 63% of controls, respectivly, 24 h after their removal. No downregulation of CPTHR binding occurred following exposure for 24 hr to hPTH(1-34) (1 μM), hPTH(39-84) (1 μM), 1,25(OH)$_2$D$_3$ (10 nM), 8-bromo cAMP (1 mM), forskolin (10 μM), insulin (100 ng/mL), IGF-1 (100 mM) or dexamethasone (100 nM).

Morphology and Gene Expression

The C cells, which had been selected for high expression of CPTHRs, exhibited a characteristic morphology, including the presence of numerous elongated dendritic processes reminiscent of those seen in mature osteocytes (FIGS. 4A and B). This stellate appearance was distinct from the more cuboidal shape of the osteoblastic ("F") cells that previously had been isolated from the same calvarial digest on the basis of high alkaline phosphatase activity (Divieti, P., et al., *J. Bone. Miner. Res.* 13:1835-1845 (1998) (FIG. 4C). Because of their osteocytic morphology, the three C cell lines were renamed "OC cells".

Others have reported that osteocytes, unlike osteoblasts, express little or no alkaline phosphatase, cbfa-1/osf-2, or collagen I but do express high levels of mRNAs for osteocalcin, Cx43 and CD44 (Kato, Y., et al., *J. Bone Miner. Res.* 12:2014-2023 (1997); Hughes, D. E., et al., *J. Bone Miner. Res.* 9:39-44 (1994)). To further define the phenotype of the osteocyte-like OC cell lines, expression of specific mRNAs characteristic of osteoblasts or osteocytes was analyzed by RT-PCR in OC cells and in murine primary calvarial osteoblasts (FIG. 5). In the OC cells (lanes "1" and "2") the expression of mRNAs for alkaline phosphatase (FIG. 5E) and cbfa-1/osf-2 (FIG. 5F) was barely detectable by RT-PCR, by comparison with that in the primary calvarial osteoblasts (lane "3"). On the other hand, OC cell expression of mRNAs for CD 44, osteocalcin, osteopontin and collagen I α (FIGS. 5 A-D) respectively, and for Cx43 was more comparable to that in primary osteoblasts. Cx43 protein was detected in all three OC cell lines by Western blot analysis and by direct immunostaining of fixed cells using anti-Cx43 antibody, which demonstrated Cx43 protein both in the cytoplasm and along the dendritic processes [FIGS. 4(A and B) and FIG. 6]. In addition, stimulation of OC cells with 100 nM hPTH(1-84) for 2 hr increased the expression of Cx43, especially in a perinuclear location, as revealed by immunostaining, (FIGS. 6B vs. 6A). A similar effect also was observed after treatment for 2 hr with 1 μM hPTH(39-84) (FIG. 6C).

The OC cells were capable of mineralization, as detected by von Kossa staining after 4 weeks in the presence of 10 mM β-glycerophosphate and 50 μg/ml of ascorbic acid (FIG. 7). Both mineralization (FIGS. 7B vs. A) and Cx43 expression (FIGS. 4B vs. A) were greatly increased when cells were maintained at 39° C., condition under which the transforming T antigen is inactive.

CPTHR Expression in Other Cells

To determine if abundant CPTHR expression is a specific characteristic of osteocytic cells or a more generalized feature of bone cells, $^{125}$I-[Tyr$^{34}$]hPTH(19-84) radioligand binding was performed with several other bone and non bone-derived cell lines. As shown in Table 1, CPTHR specific binding was much greater in the osteocytic cells than in the unfractionated original calvarial digest (F1) or the previously isolated osteoblastic (F1-14) or bone marrow stromal cells (MS1) (Liu, B. Y., et al., *Endocrinology* 139:1952-1964 (1998)). Minimal specific binding was detected on HeLa, BHK1, NIH3T3 cell or, as previously reported, on LLC-PK1 porcine kidney cells (Inomata, N., et al., *Endocrinology* 136:4732-4740 (1995)).

Apoptosis

It was shown recently that PTH(1-34), presumably acting via PTH1Rs, can reduce the rate at which osteoblasts and osteocytes undergo apoptosis in vivo and in vitro (Jilka, R. L., et al., *J. Clin. Invest.* 4:439-446 (1999); Manolagas, S. C., *Endocr. Rev.* 21:115-137 (2000)). As osteocytes are terminally differentiated osteoblasts, it was of interest to determine if CPTHR activation plays a role in regulating apoptosis in the OC cells. As shown in FIGS. 8(A and B) when OC cells, which lack functional PTH1R genes, were incubated for 6 hr with 100 nM hPTH(1-84), increased nuclear pylulosis ;aid chromatin condensation appeared, as revealed by DNA staining with Hoest dye 33258. Increased apoptosis also was observed using a TUNEL immunocytochemical assay (FIGS. 8C and D). Similarly, when cell death was monitored using trypan blue staining of combined adherent and nonadherent cells front these cultures (Jilka, R. L., et al., *J. Clin. Invest.* 4:439-446 (1999)), hPTH(1-84) induced a doubling in trypan blue-stained cells after 16 hr (FIG. 9A). This effect was mimicked by 100 nM hPTH(24-84) and 1000 nM hPTH(39-84), which produced, respectively, 1.8 and 1.5 fold increases over basal (FIGS. 9C and 9B). As expected, hPTH(1-34) was inactive, even at concentrations as high as 1000 nM, consistent with its inability to bind to CPTHR sites on these cells (FIG. 2). In these experiments, the percentage of trypan blue-stained cells in untreated controls was substantial (20-30%), perhaps because of the prolonged incubation at the nonpermissive temperature in the presence of reduced serum. The effect of hPTH(1-84) upon cell death was concentration-dependent and maximal at 10 nM, with an $EC_{50}$ in the range of 0.1 nM (FIG. 9A). Cell death triggered by hPTH(1-84) was blocked completely by prior addition of the caspase-3 inhibitor DEVD (50 μg/ml) (FIG. 9D).

Discussion

Osteocytes comprise over 90% of bone cells, yet their functions, and the involvement of systemic hormones in regulating them, are incompletely understood. Located in interconnecting lacunae deep within the mineralized matrix of bone, osteocytes are believed to fulfill an important mechanosensory function, whereby they transduce shear and strain forces into chemical signals that communicate this information to other osteocytes, osteoblasts and, ultimately, osteoclasts (Manolagas, S. C., *Endocr. Rev.* 21:115-137 (2000); Mullender, M. G., et al., *Bone* 20:527-532 (1997); Klein-Nulend, J., et al., *Biochem. & Biophys. Res. Comm.* 217:640-648 (1995)). Osteocytes express PTH1Rs, and their response to mechanical forces in vivo is enhanced by, and may even require, circulating PTH (van der Plas, A., et al., *J. Bone Miner. Res.* 9:1697-1704 (1994)).

It is presently shown that clonal murine calvarial-derived cell lines with many characteristics of osteocytes also express unusually large numbers of receptors that specifically recognize the C-terminal portion of intact PTH. In fact, these cells express considerably higher levels of CPTHRs (up to ten-fold more per cell) than do other bone cell subtypes, including mature osteoblasts (Divieti, P., et al., *J. Bone. Miner. Res.* 13:1835-1845 (1998)). It is difficult to identify the osteocytic phenotype with complete confidence in vivo, absent the normal surrounding lacunar environment, but the three conditionally immortalized, clonal cell lines that were selected exclusively on the basis of high CPTHR expression share many morphological features and a distinctive profile of gene expression with normal osteocytes (Nijweide, P. J., et al., "The Osteocyte," in *Principle of Bone Biology,* Bilezikian, J. P., et al., (eds.), Academic Press, New York, N.Y., pp. 115-126 (1996)) and with a previously characterized osteocytic cell line (Kato, Y., et al., *J. Bone Miner. Res.* 12:2014-2023 (1997)). These include a stellate shape, with numerous dendritic processes, and abundant expression of mRNAs for osteocalcin, Cx43, and CD44 but not for alkaline phosphatase or osf-2/cbfa-1, which are more characteristic of early or mature osteoblasts. The osteocytic phenotype of these cells is most intense when they are maintained at a temperature (i.e., 39° C.) that is nonpermissive for expression of functional transforming tsTAg. For example, both mineralization (FIG. 7) and Cx43 expression, detected immunohistochemically (FIG. 4), were more evident after maintaining these cells for several days at 39° C. than at 33° C. This pattern is consistent with previous work with other clonal bone cells that express this tsTAg (Divieti, P., et al., *J. Bone. Miner. Res.* 13:1835-1845 (1998); Liu, B. Y., et al., *Endocrinology* 139:1952-1964 (1998)).

The OC cells were isolated purposely from animals that genetically lack functional PTH1Rs in order to eliminate possible confounding effects of co-expressed PTH1Rs and to allow direct focus upon CPTHR-dependent actions of intact PTH. The results of radioreceptor binding assays in OC cells, using the $^{125}$I-[Tyr$^{34}$]hPTH(19-84) radioligand, were remarkably similar to those reported previously with ROS17/2.8 cells (Inomata, N., et al., *Endocrinology* 136: 4732-4740 (1995); Takasu, H., et al., *Endocrinology* 137: 5537-5543 (1996)), which suggests that the CPTHRs on these different cell types probably are similar or identical. Thus, like Inomata et al., it has been found that hPTH(1-84) and the hPTH(19-84) peptide bound equivalently to CPTHRs and that hPTH(39-84) bound more weakly, with an $IC_{50}$ roughly 15-fold higher. The ligand domain responsible for this higher affinity interaction has further been narrowed, moreover, by studying hPTH(24-84), which was found to bind at least as well as hPTH(1-84). This indicates that CPTHRs require sequences within the region hPTH(24-38) for high affinity binding, although other, more C-terminal domains also must be involved to account for the residual affinity of hPTH(39-84). In fact, it seems likely that sequences C-terminal to residue 39 may be absolutely required for CPTHR binding, as hPTH(1-34) contains most of the region hPTH(19-39) and yet cannot effectively displace the $^{125}$I-[Tyr$^{34}$]hPTH(19-84) radioligand from CPTHR sites on the OC cells, even at very high concentrations. Enumeration of CPTHR sites on the OC cells led to estimates of 1,900,000 to 3,400,000 per cell, which was 5 to 10-fold higher than on the osteoblastic (F) cells obtained from the same bones, and at least 5-fold higher than on ROS 17/2.8 cells (Inomata, N., et al., *Endocrinology* 136:4732-4740 (1995)). A survey of other available cell lines indicated that, with the exception of a bone marrow stromal cell line (MS-1) (Liu, B. Y., et al., *Endocrinology* 139:1952-1964 (1998)), little or no binding was detectable on NIH-3T3, HeLa or BHK21 fibroblast cells, as was reported previously for OK and LLC-PKI kidney cells, YCC cells, and SaOS-2, MG63 and UMR106-01 osteosarcoma cells (Inomata, N., et al., *Endocrinology* 136:4732-4740 (1995)). Thus, the very high abundance of expressed CPTHRs on osteocytic OC cells is unique, even among other bone cells tested, and suggests that these receptors may play an important role in osteocyte regulation. The possibility that bone is an important C-PTH target tissue is further supported by recent observation that $^{125}$I-[Tyr$^{34}$]hPTH(19-84) radioligand binds specifically to frozen sections of 18.5-day normal mouse fetal calvarial bone and that hPTH(7-84) reduces the calcemic effects of intact PTH(1-84) in vivo at concentrations much lower than those required for effective antagonism of the PTH1R (Slatopolsky, E., et al., "A Novel Mechanism for Skeletal Resistance in Uremia," in *Program of the American Society of Nephrology Annual Meeting,* Miami, Fla. (Abstract) (1999)).

Functional studies of CPTHRs on OC cells have pointed so far to involvement in at least two general types of cellular processes: cell survival and intercellular communication. A powerful effect of CPTHR-interacting ligands has been observed to increase the rate of cell death in vivo. As this action was accompanied by evidence of increased nuclear pyknosis, chromatin condensation and TUNEL staining and was completely blocked by the caspase-3 inhibitor DEVD, it is concluded that apoptosis, mediated by activation of the caspase cascade, is the likely mechanism. Importantly, this pro-apoptotic effect was observed also with the C-terminal fragment hPTH(39-84) (at an appropriately higher concentration), which indicates that the ligand domain required for CPTHR activation likely is located C-terminal to the above-mentioned hPTH(24-38) region needed for high-affinity binding. CPTHRs may play a physiologic role in controlling osteocyte survival and that excessive CPTHR activation, as may occur in renal insufficiency, could lead to exaggerated, pathological loss of osteocytes and contribute to some forms of renal osteodystrophy (Bonucci, E., and Gherardi, G., *Virch. Arch.* 373:213-231 (1977)).

It has also been found that CPTHR ligands rapidly increased expression of Cx43, a gap-junction protein believed to be important in mediating communication and previously shown to be expressed by both osteoblasts and osteocytes (Civitelli, R., et al., *J. Clin. Invest.* 91:1888-1896 (1993); Ziambaras, K., et al., *J. Bone Miner. Res.* 13:218-228 (1998)). The possible physiologic significance of this response is not yet clear. The response of osteocytes to mechanical stress in vivo was shown to be promoted by PTH(1-34) and blocked by parathyroidectomy (Chow, J. W., et al., *Am. J. Physiol.* 274:E146-E154 (1998)). Given that C-PTH fragments are preferentially secreted by the parathyroids during hypercalcemia (D'Amour, P., et al., *Am. J. Physiol.* 251:E680-E687 (1986)), it seems possible that CPTHR activation on osteocytes could foster intercellular communication among osteocytes and osteoblasts that ultimately might reduce osteoclast formation or activity. Availability of osteocytic cell lines now should make it possible to test such hypotheses, even if indirectly and in vitro.

Expression of the PTH1R by osteocytes has been documented in vivo (Lee, K., et al., *Bone* 14:341-345 (1993)), and it is of interest to consider the potential for interactions between PTH1Rs and CPTHRs in these cells. It is possible that the genetic absence of PTH1R in the OC cells may have modified in some way the expression or function of CPTHRs. Almost certainly, the response of these PTH1R-null cells to hPTH(1-84) in vitro differs from that of authentic osteocytes in vivo, in which both receptor types presumably can be activated concurrently by the intact hormone. There is preliminary evidence, in ROS 17/2.8 cells, that C-PTH fragments may modify the function of hPTH(1-84) (but not hPTH(1-34)) in cells that express both types of PTH receptors (D'Amour, P., et al., *J. Bone Miner. Res.* 12:S318 (1997)). The possible involvement of PTH1Rs in modulating CPTHR function, or vice versa, now can be addressed directly in the OC cells by reconstituting them through transfection with cDNA encoding, PTH1Rs; efforts in this direction are underway.

Finally, the molecular nature and signaling properties of the CPTHR(s) are unknown, although it is clear that they do not couple effectively to Gs/adenylyl cyclase. Homologous downregulation of surface CPTHR binding by hPTH(1-84) was observed that could be mimicked by ionomycin and phorbol ester. Others have reported cytosolic calcium transients, due to activation of calcium influx via nickel-insensitive channels, during exposure of human fetal chondrocytes to C-PTH peptides in vitro (Erdmann, S., et al., *J. Cell Biol.* 135:1179-1191 (1996)). Further study of the possible involvement of calcium movements in CPTHR signaling in OC cells is underway.

TABLE 1

CPTHR binding in various cell lines

| Cell line | Total binding (% TC) | Specific Binding (% TC) |
|---|---|---|
| OC 59 | 11.9 ± 1.2 | 10.2 ± 2.8 |
| F1 | 4.1 ± 1.4 | 2.8 ± 2.5 |
| F1-14 | 3.2 ± 0.3 | 2.4 ± 1.7 |
| MS-1 | 2.9 ± 0.1 | 2.1 ± 0.1 |
| NIH-3T3 | 1.6 ± 0.2 | 0.6 ± 0.2 |
| HeLa | 0.9 ± 0.1 | 0.5 ± 0.1 |
| BHK21 | 0.6 ± 0.1 | 0.4 ± 0.1 |

Data shown were obtained from experiments in which total cpm of $^{125}$[Tyr$^{34}$]hPTH(19-84) added ("TC") ranged between 66,000 and 140,000 cpm/well. Values shown are means ± SD for triplicates. Specific binding was obtained after subtraction of radioligand bound in the presence of 1000 nm hPTH(1-84).

EXAMPLE 2

Radioreceptor studies of PTH1R-null, CPTHR-expressing calvarial-derived clonal cells, conducted with [Tyr$^{34}$]$^{135}$I-hPTH(19-84) and competing amino (N)-terminally truncated fragments of hPTH(1-84) implicates two key binding domains within two highly conserved regions which includes Leu$^{24}$-Arg$^{25}$-Lys$^{26}$-Lys$^{27}$, and Lys$^{53}$-Lys$^{54}$. To further investigate the importance of these determinants, radioreceptor assays (see Example 1) were performed using short synthetic peptides, i.e., hPTH(20-30), hPTH(50-60), and hPTH(24-54), that span either one or both of these domains. hPTH(20-30) and hPTH(50-60), either alone or in combination, failed to bind to the CPTHR, whereas hPTH(24-54) was able to compete the [Tyr$^{34}$]$^{135}$I-hPTH(19-84) tracer, with an apparent $EC_{50}$ of 20,000 nM. Higher resolution analysis, using Ala-substituted versions of these peptides, showed that substitutions in positions 25 and 53 dramatically impaired binding affinity, while substitutions in positions 24, 26, 27 or 54 were better tolerated. These results indicate that the domains comprising hPTH(24-27) and hPTH(53-54) do not function independently and that the basic residues Arg$^{25}$ and Lys$^{53}$ are critical for effective interaction of hPTH with CPTHRs in bone-derived cells.

All documents, e.g., scientific publications, patents and patent publications recited herein are hereby incorporated by reference in their entirety to the same extent as if each individual document was specifically and individually indicated to be incorporated by reference in its entirety. Where the document cited only provides the first page of the document, the entire document is intended, including the remaining pages of the document.

What is claimed is:

1. An isolated osteocyte lacking type-1 parathyroid hormone (PTH)/parathyroid hormone-related peptide (PTHrP) receptor (PTH1R) activity and containing carboxyl-terminal parathyroid hormone receptor (CPTHR) activity.

2. The cell of claim 1, wherein said osteocyte is homozygous for the ablation of the PTH1R gene.

3. A method of screening for agonists or antagonists for carboxyl-terminal parathyroid hormone receptor (CPTHR), said method comprising:

(a) contacting an isolated osteocyte lacking type-1 parathyroid hormone (PTH)/parathyroid hormone-related peptide (PTHrP) receptor (PTH1R) activity and containing CPTHR activity with a candidate compound; and (b) determining the rate of apoptosis of said cell, wherein an accelerated rate of apoptosis compared to said osteocyte not contacted with a candidate compound indicates that said compound is an agonist for CPTHR, and wherein a rate of apoptosis equal to or less than said osteocyte not contacted with a candidate compound indicates that said compound is an antagonist for CPTHR.

4. The method of claim 3, wherein said osteocyte is homozygous for the ablation of the PTH1R gene.

* * * * *